United States Patent
Li et al.

(10) Patent No.: US 9,795,351 B2
(45) Date of Patent: Oct. 24, 2017

(54) THREE-DIMENSIONAL CARDIAC IMAGE SEGMENTATION METHOD AND APPARATUS

(71) Applicant: Shenyang Neusoft Medical Systems Co., Ltd., Shenyang (CN)

(72) Inventors: Bingsheng Li, Shenyang (CN); Wei He, Shenyang (CN)

(73) Assignee: SHENYANG NEUSOFT MEDICAL SYSTEMS CO., LTD., Shenyang (CN)

(*) Notice: Subject to any disclaimer, the term of this patent is extended or adjusted under 35 U.S.C. 154(b) by 89 days.

(21) Appl. No.: 14/830,754

(22) Filed: Aug. 20, 2015

(65) Prior Publication Data
US 2016/0051214 A1   Feb. 25, 2016

(30) Foreign Application Priority Data

Aug. 20, 2014   (CN) .......................... 2014 1 0413009

(51) Int. Cl.
*G06K 9/00*  (2006.01)
*A61B 6/00*  (2006.01)
(Continued)

(52) U.S. Cl.
CPC ............ *A61B 6/503* (2013.01); *A61B 6/5211* (2013.01); *G06T 7/12* (2017.01); *G06T 7/149* (2017.01);
(Continued)

(58) Field of Classification Search
CPC ..................................................... A61B 6/503
See application file for complete search history.

(56) References Cited

U.S. PATENT DOCUMENTS

| 5,889,524 A | 3/1999 | Sheehan et al. |
| 2008/0123914 A1 | 5/2008 | De Bliek et al. |

(Continued)

FOREIGN PATENT DOCUMENTS

| CN | 101065775 A | 10/2007 |
| CN | 102397070 A | 4/2012 |

(Continued)

OTHER PUBLICATIONS

Vadakkumpadan et al (NPL Image based models of cardiac structure in health and disease, NIH Public Access, p. 33, Wiley Interdiscip Rev Syst Biol Med. Jul. 2010 ; 2(4): 489-506. doi:10.1002/wsbm. 76).*

(Continued)

*Primary Examiner* — Oneal R Mistry
(74) *Attorney, Agent, or Firm* — Kilpatrick Townsend & Stockton LLP (57) ABSTRACT

A three-dimensional cardiac image segmentation method and apparatus are provided according to examples of the present disclosure. The method includes: searching from layers of cardiac computerized tomography CT images to obtain a layer of cardiac CT image located between a heart bottom portion and a heart upper portion as a first key layer; searching on the first key layer to obtain a boundary of the heart as a contour of the heart bottom portion, and generating a curved surface model based on the contour of the heart bottom portion and a lowest point of the heart bottom portion as a heart bottom model; searching layers of cardiac CT images above the first key layer to obtain boundaries of the heart as a contour of the heart upper portion, and generating a curved surface model based on the contour of the heart upper portion as a heart upper model.

19 Claims, 7 Drawing Sheets

(51) Int. Cl.
 G06T 7/12       (2017.01)
 G06T 7/149      (2017.01)
 G06T 7/174      (2017.01)
 A61B 6/03       (2006.01)

(52) U.S. Cl.
 CPC .............. *G06T 7/174* (2017.01); *A61B 6/032* (2013.01); *G06T 2207/10081* (2013.01); *G06T 2207/20116* (2013.01); *G06T 2207/30048* (2013.01)

(56) References Cited

U.S. PATENT DOCUMENTS

| | | | |
|---|---|---|---|
| 2008/0181481 A1* | 7/2008 | Hong | G06T 7/12 382/132 |
| 2008/0292169 A1 | 11/2008 | Wang et al. | |
| 2012/0134564 A1* | 5/2012 | Zheng | G06T 7/0081 382/131 |
| 2015/0035829 A1* | 2/2015 | Miyamoto | A61B 5/055 345/423 |
| 2015/0045662 A1* | 2/2015 | Kim | A61B 8/0883 600/427 |

FOREIGN PATENT DOCUMENTS

| | | |
|---|---|---|
| CN | 102663824 A | 9/2012 |
| CN | 103985124 A | 8/2014 |

OTHER PUBLICATIONS

First Office Action dated Aug. 1, 2016 from the State Intellectual Property Office of People's Republic of China for Appln. No. 201410413009.5, 14 pages.

\* cited by examiner

THREE-DIMENSIONAL CARDIAC IMAGE SEGMENTATION METHOD AND APPARATUS

This application claims priority to Chinese Patent Application No. 201410413009.5, titled "THREE-DIMENSIONAL CARDIAC IMAGE SEGMENTATION METHOD AND APPARATUS", filed with the Chinese State Intellectual Property Office on Aug. 20, 2014, which is incorporated by reference in its entirety herein.

BACKGROUND

According to statistics, coronary heart disease (a full name is coronary atherosclerotic heart disease) is one of major diseases seriously impacting on human health, and its incidence has been increased in recent years. Therefore, it is of great importance to detect, diagnose and treat the coronary heart disease early. The early detection of the coronary heart disease mainly depends on a three-dimensional cardiac image of a patient. Therefore, a method for obtaining the three-dimensional cardiac image of the patient is critical in the early detection of the coronary heart disease.

The heart, which acts as a power source of a human body's circulatory system, is one of the most important organs of the human body. The heart is located within the chest, above the diaphragm and between the two lungs, with the front of the heart neighboring the anterior wall of the chest. Therefore, adjacent tissues of the heart, such as air, the lungs, the diaphragm, a descending aorta, a pulmonary artery, a pulmonary vein and an auricular appendix, are required to be removed from the three-dimensional cardiac image to display the heart, an ascending aorta and a coronary visually clearly, so that the morphology of the ascending aorta, coronary tree and chambers can be checked conveniently.

At present, there are several three-dimensional cardiac image segmentation methods. The most common method is a segmentation method based on traditional region growing. In the region growing segmentation method, the affects of noise and morphology of the neighboring tissues of the heart are not fully taken into account, hence over-segmentation or under-segmentation is prone to occur, which may lead to low accuracy of the segmentation. For example, a left anterior descending coronary artery which is adjacent to the sternum is often removed by using the region growing segmentation method. As another example, a bottom of the heart is connected with the diaphragm, and the boundary between the heart and the diaphragm is not easily distinguishable, therefore the diaphragm is difficult to be removed completely by using the region growing segmentation method, which may affect the observation of a right coronary artery and a posterior descending branch.

Besides the region growing segmentation method, a common method is a training-based segmentation method with higher accuracy compared with the conventional region growing segmentation method. In this segmentation method, a large amount of three-dimensional cardiac data are used for repeat training to obtain an original three-dimensional heart model, and then some processing such as deformation, smoothing processing or segmentation processing are performed on the original three-dimensional heart model to obtain a three-dimensional cardiac image. This segmentation method depends on the original three-dimensional heart model, and the establishment of the model must take repeated training, therefore the computation amount and complexity of segmentation are increased, and it is difficult to achieve fast image segmentation.

Therefore, it is highly required an effective three-dimensional cardiac image segmentation scheme, to improve the segmentation accuracy, or reduce the computation amount and complexity of segmentation, thereby enabling fast image segmentation.

BRIEF DESCRIPTION OF THE DRAWINGS

FIG. 4-1 is a three-dimensional schematic diagram of a rear segment of the heart bottom model according to an example of the present disclosure;

FIG. 4-2 is a three-dimensional schematic diagram of a front segment and a middle segment of the heart bottom model according to an example of the present disclosure;

DETAILED DESCRIPTION OF THE EXAMPLES

A three-dimensional cardiac image segmentation method and apparatus are provided according to examples of the present disclosure. Considering morphology of a heart is complicated, i.e., there is a distinguishable boundary between a top of the heart and neighboring tissues, however, a bottom of the heart is connected with a diaphragm. Both the bottom of the heart and the diaphragm have a similar gray scale and there is no obvious boundary between them, thus it is difficult to perform a cardiac image segmentation. Therefore, in the examples of the present disclosure, firstly, a key layer between a heart bottom portion and a heart upper portion is located, and the heart is segmented into an upper portion and a bottom portion based on the key layer, then, a heart upper model and a heart bottom model are established; finally, a whole three-dimensional heart model including the heart upper model and the heart bottom model is formed. According to the disclosure, a three-dimensional cardiac image may be illustrated clearly with the three-dimensional heart model.

In order for clarity of the disclosure, some examples of the disclosure are illustrated in detail in conjunction with the drawings.

Figure 1:
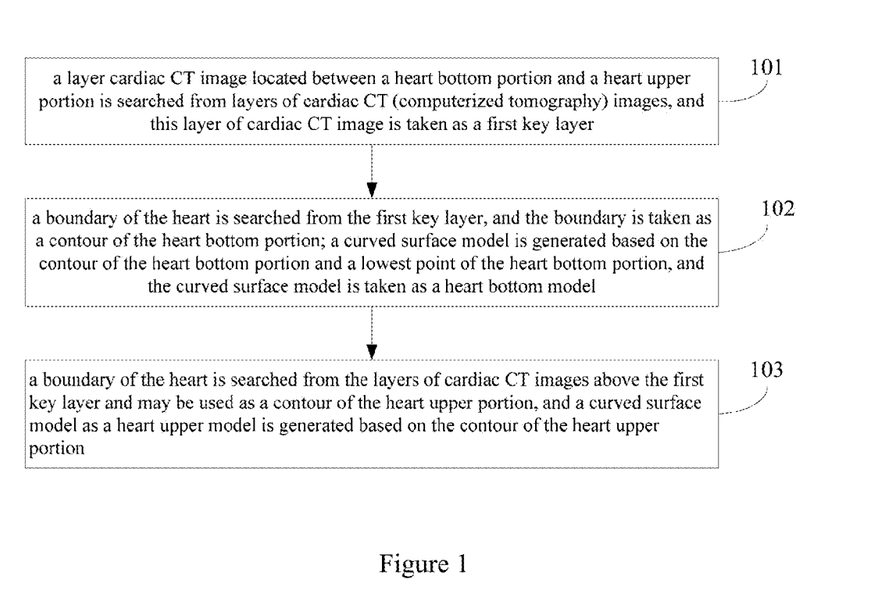
FIG. 1 is a flow chart of a three-dimensional cardiac image segmentation method according to an example of the present disclosure.

FIG. 1 is a flow chart of a three-dimensional cardiac image segmentation method according to an example of the present disclosure, and the method includes:

Block 101, a layer cardiac CT image located between a heart bottom portion and a heart upper portion is searched from layers of cardiac CT (computerized tomography) images, and this layer of cardiac CT image is taken as a first key layer.

According to an example of the present disclosure, the first key layer may be obtained by the following blocks. A heart center point is located in the layers of cardiac CT images. Line-by-line scanning is performed on a coronal image where the heart center point is located, and whether a lung is detected in a scanned line is determined; a next line is scanned in the case that the lung is detected in the scanned line, or the scanning is stopped in the case that no lung is detected in the scanned line. The layer of CT image containing a scanned line where the scanning is stopped is determined as the first key layer between the heart bottom portion and the heart middle portion.

Figure 2:
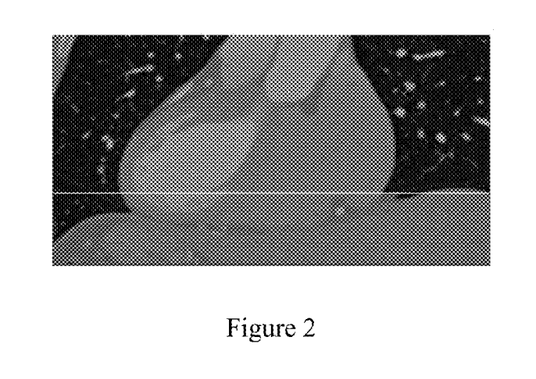
FIG. 2 is a schematic diagram of determining a key layer on a scanned coronal image where the heart center point is located according to an example of the present disclosure.

The heart bottom portion is connected with the diaphragm. Therefore, in an example of the present disclosure, the heart bottom portion is located based on key points between the heart and the lungs. For example, line-by-line scanning is performed from top to bottom on a coronal image (a transverse cross-sectional image containing the scanned line is located is defined a layer of cardiac CT image) as shown in FIG. 2. It is determined whether a lung is detected in a scanned line. The scanning is stopped in the case that no lung is detected in the scanned line. It is considered that the diaphragm is scanned in the case that the lung is not detected. A transverse cross-sectional image containing the scanned line where the scanning is stopped is determined as the first key layer between the heart bottom portion and the heart middle portion.

In some examples of the disclosure, instead of the heart center point, a ventricular top point may be located. Further, in stead of the lungs, the diaphragm may be detected. That is, it is determined whether the diaphragm is detected in a scanned line. A next line is scanned in the case that the diaphragm is not detected, or the scanning is stopped in the case that the diaphragm is detected.

The heart is connected with an aorta and lies between two lungs. Therefore, the heart center point may be located based on a position of the ascending aorta or a midpoint of the two lungs.

According to an example of the present disclosure, a process of locating the heart center point based on the position of the ascending aorta may include: detecting an ascending aorta from the layers cardiac CT images obtained after aortography; and determining a lowest center point of the ascending aorta, taking the lowest center point of the ascending aorta as a position of a heart valve and marking the position of the heart valve as the heart center point.

For example, the aorta starts from the left ventricle and extends up to an aortic arch. A thorough channel inside the aorta facilitates aortography. After the aortography, the aorta can be obviously displayed on the layers of cardiac CT images. Since a cross section of the ascending aorta is nearly circular, the ascending aorta can be recognized from the aorta in layers of cardiac CT image by using a circle detection method and a clustering method. And the center point of the ascending aorta can be determined. A series of center points of the ascending aorta can be obtained from the layers of cardiac CT images, and the lowest center point of the ascending aorta is marked as a position of a heart valve. The position of the heart valve is the desired heart center point in this example.

According to another example of the present disclosure, the process of locating the heart center point based on the position of two lungs may include: detecting a left lung and a right lung on the layers of cardiac CT images; and calculating distances between the left lung and the right lung, selecting the longest distance between the left lung and the right lung, determining a midpoint of the longest distance as a position of a heart valve, and marking the position of the heart valve as the heart center point.

For example, both lungs have uniform gray scale and regular morphology, therefore both the right lung and left lung can be detected from each layer of cardiac CT image by using a threshold segmentation method or a directional region growing segmentation method. A series of distances between the left lung and the right lung can be obtained from the layers of cardiac CT images, and the longest distance between the left lung and the right lung can be selected. Finally a midpoint of the longest distance can be determined as a position of the heart valve.

Block 102, a boundary of the heart is searched from the first key layer, and the boundary is taken as a contour of the heart bottom portion; a curved surface model is generated based on the contour of the heart bottom portion and a lowest point of the heart bottom portion, and the curved surface model is taken as a heart bottom model.

For example, an optimal-cost path between each sampling point on the contour of the heart bottom portion and the lowest point of the heart bottom portion may be calculated, and a curved surface model as a heart bottom model may be generated based on the optimal-cost path. Alternatively, an optimal-cost path between each pair of sampling points on the contour of the heart bottom portion and symmetrical in coronal direction may be calculated, and a curved surface model as the heart bottom model may be generated based on the optimal-cost path.

Considering the morphology of the heart bottom portion, generally, the contour of the heart bottom portion is difficult to be located since a part of the heart bottom portion has no indistinct border with the sternum; another part of the heart bottom portion neighbors the left lung and the right lung; and yet another part of the heart bottom portion is adjacent to the descending aorta and the vertebral.

Therefore, the contour of the heart bottom portion may be segmented into a front segment, a middle segment and a rear segment, and the front segment, the middle segment and the rear segment of the contour of the heart bottom portion may be processed in various ways.

Figure 3:
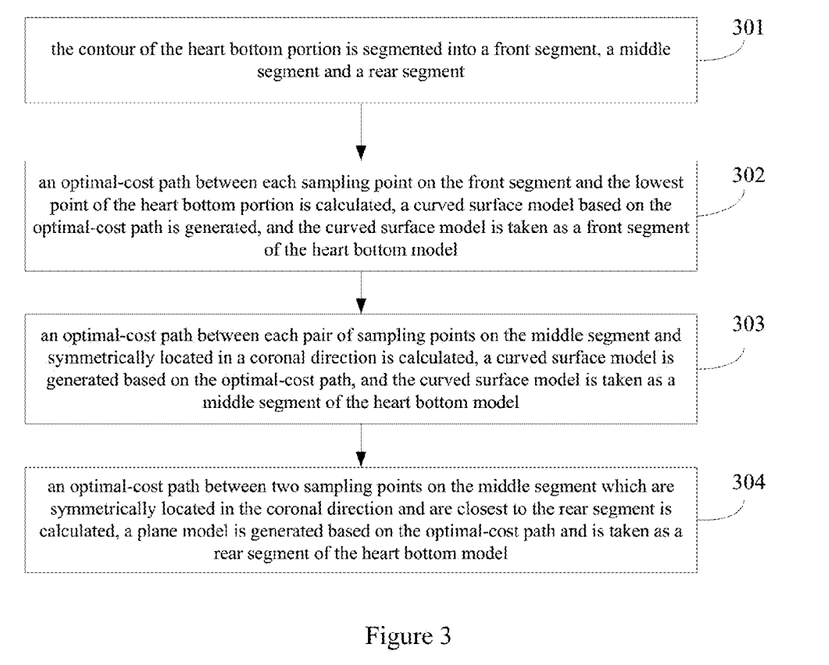
FIG. 3 is a flow chart of a process of generating a heart bottom model based on a contour of a heart bottom portion and a lowest point of the heart bottom according to an example of the present disclosure.

As shown in FIG. 3, according to an example of the present disclosure, a curved surface model to be used as the heart bottom model may be generated based on the contour of the heart bottom portion and the lowest point of the heart bottom portion. The method includes blocks 301 to 304.

Block 301, the contour of the heart bottom portion is segmented into a front segment, a middle segment and a rear segment.

Block 302, an optimal-cost path between each sampling point on the front segment and the lowest point of the heart bottom portion is calculated, a curved surface model based on the optimal-cost path is generated, and the curved surface model is taken as a front segment of the heart bottom model.

Block 303, an optimal-cost path between each pair of sampling points on the middle segment and symmetrically located in a coronal direction is calculated, a curved surface model is generated based on the optimal-cost path, and the curved surface model is taken as a middle segment of the heart bottom model.

Block 304, an optimal-cost path between two sampling points on the middle segment which are symmetrically located in the coronal direction and are closest to the rear segment is calculated, a plane model is generated based on the optimal-cost path and is taken as a rear segment of the heart bottom model.

The lowest point of the heart bottom portion is located at the lowest t bottom of the heart. Multiple optimal-cost paths of the contour of the heart middle portion may be generated in the coronal direction, and each of the optimal-cost paths has a lowest point. A lowest point selected from of the lowest points of the optimal-cost paths neighboring the sternum is taken as the lowest point of the heart bottom portion.

Figure 41:
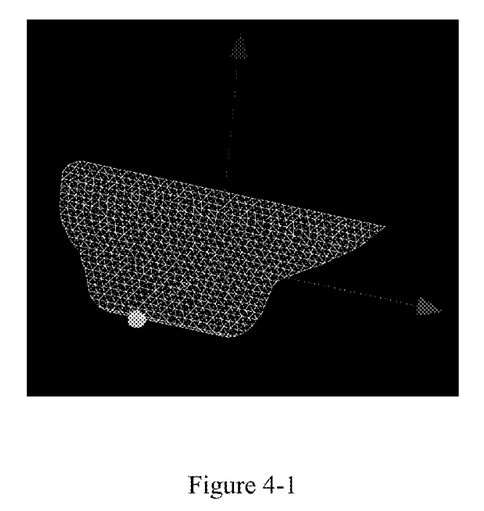
Figure 42:
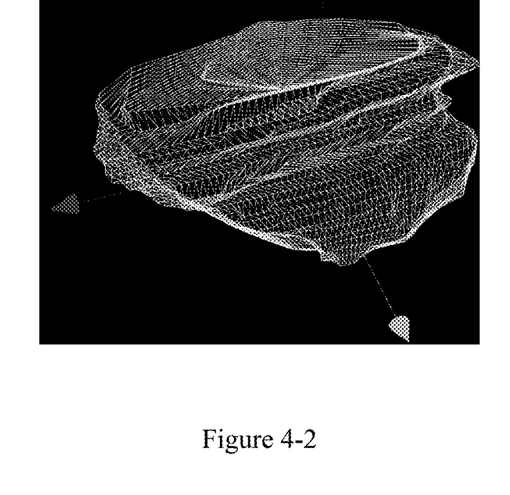

FIG. 4-1 is a three-dimensional schematic diagram of a rear segment of the heart bottom model according to an example of the present disclosure, and FIG. 4-2 is a three-dimensional schematic diagram of a front segment and a middle segment of the heart bottom model according to an example of the present disclosure.

Block 103, a boundary of the heart is searched from the layers of cardiac CT images above the first key layer and may be used as a contour of the heart upper portion, and a curved surface model as a heart upper model is generated based on the contour of the heart upper portion.

To establish a three-dimensional heart model closer to a real situation, the heart upper portion may be further segmented into a heart top portion and a heart middle portion, and a heart top model and a heart middle model may be generated respectively.

Therefore, according to an example of the present disclosure, the above-mentioned method may further include: searching a layer cardiac CT images between the heart top portion and the heart middle portion from the layers of scanned cardiac CT images; and taking the cardiac CT image as the second key layer.

The above-mentioned block 103 may include: searching on the second key layer to obtain a boundary of the heart, taking the boundary as a contour of the heart top portion, generating a plane model based on the contour of the heart top portion, and taking the plane model as a heart top model; searching layers of cardiac CT images between the first key layer and the second key layer to obtain the boundaries of the heart, taking the boundaries as the contour of the heart middle portion, generating a curved surface model based on the contour of the heart middle portion, and taking the curved surface model as a heart middle model.

According to an example of the present disclosure, the second key layer may be searched by the following steps: locating a heart center point in the layers of cardiac CT images; and determining a cardiac CT image containing the heart center point as the second key layer between the heart top portion and the heart middle portion.

Figure 5:
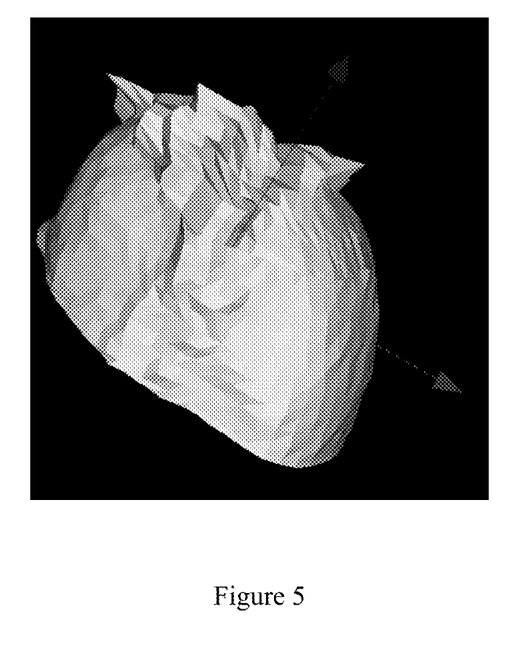
FIG. 5 is a three-dimensional schematic diagram of a heart middle model according to an example of the present disclosure.

FIG. 5 is a three-dimensional schematic diagram of a heart middle model according to the present disclosure.

In an example of the present disclosure, it may be determined firstly whether a coronary tree may be extracted; in the case that the coronary tree can be extracted, the contour of the heart upper portion are preferably segmented into the contour of the heart top portion and the contour of the heart middle portion, then the heart top model and the heart middle model are generated based on the contour of the heart top portion and the contour of the heart middle portion respectively; in the case that the coronary tree can not be extracted, only a heart upper model is generated based on the contour of the heart upper portion.

It should also be understood that, according to the present disclosure, tissues neighboring the heart bottom portion, such as air, lungs, the sternum, the descending aorta may be segmented using a segmentation method such as the region growing method, and marked in advance in the cardiac CT images. In this way, a boundary of the heart as a contour of the heart bottom portion in the first key layer can be found based on the previously marked tissues neighboring the heart bottom portion.

Tissues neighboring the heart top portion such as the ascending aorta and the atrium may also be segmented and marked previously on the second key layer. A boundary of the heart as a contour of the heart top portion can be found based on the previously marked tissues neighboring the heart top portion. And tissues neighboring the heart middle portion such as lungs, the sternum and the descending aorta may also be segmented and marked previously on layers of cardiac CT images between the first key layer and the second key layer, and then the boundaries of the heart as the contour of the heart middle portion can be found based on the previously marked tissues neighboring the heart middle portion.

According to the above examples, the present disclosure may have following advantages: a repeated training is not necessary for a three-dimensional heart model, and three-dimensional heart model is established segment by segment based on morphology of the heart. Firstly, a key layer between a heart bottom portion and a heart upper portion is located, and the heart is segmented into an upper portion and a bottom portion by the key layer. Then, a heart upper model and a heart bottom model are established. Finally, a whole three-dimensional heart model including the heart upper model and the heart bottom model is formed. Thus a three-dimensional cardiac image may be illustrated clearly with the three-dimensional heart model. According to the present disclosure, the three-dimensional cardiac image segmentation method may be resistant to local noises. Thus the segmentation accuracy is improved. The computation and complexity of segmentation may be reduced, thereby enabling fast image segmentation.

Figure 6:
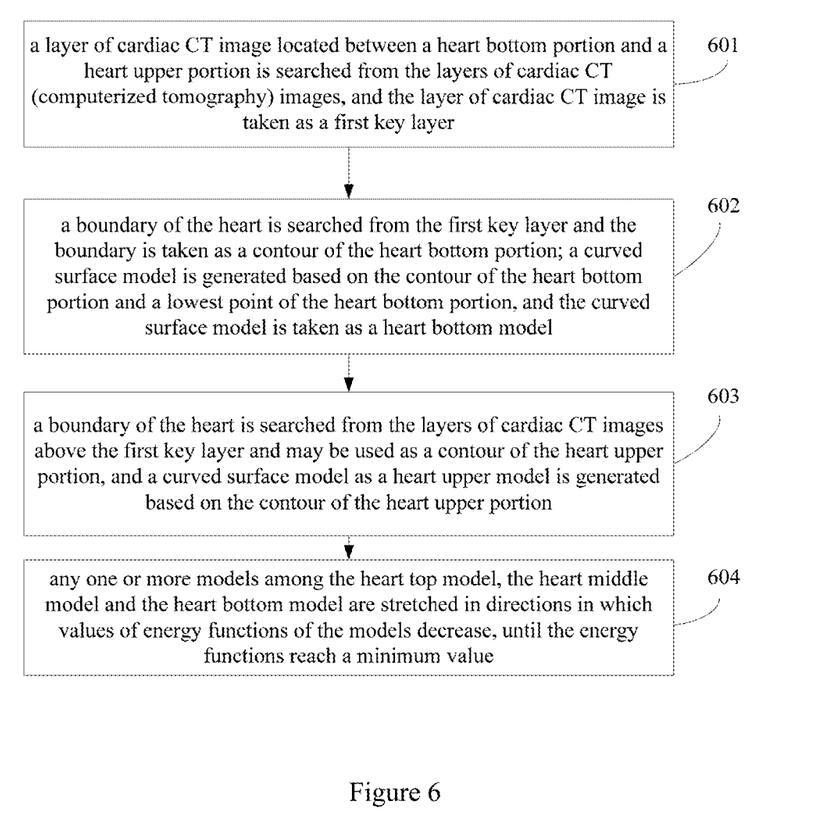
FIG. 6 is a flow chart of a three-dimensional cardiac image segmentation method according to another example of the present disclosure.

To enable the contour of said heart model to better approximate the real heart contour, stretching may be performed on each model to further effectively remove tissues such as the diaphragm, the sternum, and the spinal. FIG. 6 is a flow chart of a three-dimensional cardiac image segmentation method according to an example of the present disclosure, and the method includes:

Block 601, a layer of cardiac CT image located between a heart bottom portion and a heart upper portion is searched from the layers of cardiac CT (computerized tomography) images, and the layer of cardiac CT image is taken as a first key layer.

Block 602, a boundary of the heart is searched from the first key layer and the boundary is taken as a contour of the heart bottom portion; a curved surface model is generated based on the contour of the heart bottom portion and a lowest point of the heart bottom portion, and the curved surface model is taken as a heart bottom model.

Block 603, a boundary of the heart is searched from the layers of cardiac CT images above the first key layer and may be used as a contour of the heart upper portion, and a curved surface model as a heart upper model is generated based on the contour of the heart upper portion.

Block 604, any one or more models among the heart top model, the heart middle model and the heart bottom model are stretched in directions in which values of energy functions of the models decrease, until the energy functions reach a minimum value.

In an example, the energy function includes an internal energy function and an external energy function. Wherein the internal energy function controls the smoothness and continuity of each model, and the external energy function controls convergence of displayed targets of each model. The external energy function includes image energy and constraint energy.

Stretching is performed by means of an external force from the surrounding region and an internal force from the model itself in the direction in which the energy function of the model decreases, and the contour of the model converges to the real boundary when the energy function of the model reaches a minimum value.

The heart bottom model can be stretched in any direction, the heart middle model can be stretched in a traverse direction, and the heart top model can be stretched upwards.

According to an example of the present disclosure, besides the heart top model can be stretched according to the energy function, a region of the heart top model where a left atrium and a coronary artery are located may be stretched upwards, and the stretching of said region is stopped in the case that top boundaries of the left atrium and the coronary artery are reached.

According to another example of the present disclosure, before a value of the energy function of the heart middle model reaches the minimum value, it is determined whether the heart middle model is stretched to a position where any one of air, a lung, a sternum, or a descending aorta is located, and the stretching of the heart middle model is stopped in the case that the heart middle model is stretched to the position where any one of the air, the lung, the sternum, or the descending aorta is located.

According to another example of the present disclosure, before a value of the energy function of heart bottom model reaches the minimum value, it is determined whether the heart bottom model is stretched to a position where any one of a descending aorta or a lung is located, and the stretching of the heart bottom model is stopped in the case that the heart bottom model is stretched to the position where any one of the descending aorta or the lung is located. In this way, the surrounding tissues such as an auricular appendix, a pulmonary vein, a pulmonary artery and a superior vena cava can be removed effectively.

It should be understood that a smoothing process and a filling process may be performed on any one or more of the heart top model, the heart middle model and the heart bottom model after the stretching is performed.

Figure 7:
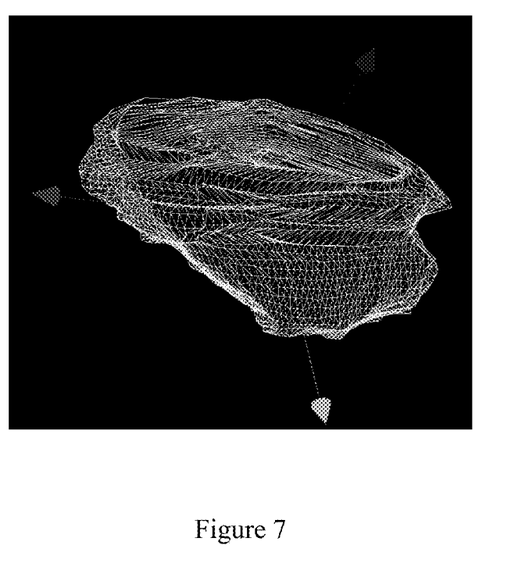
FIG. 7 is a three-dimensional schematic diagram of a front segment and a middle segment of the heart bottom model that have been stretched according to an example of the present disclosure.
Figure 8:
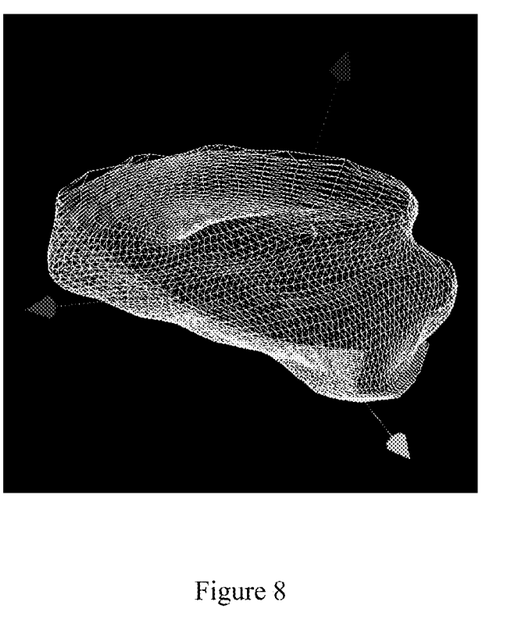
FIG. 8 is a three-dimensional schematic diagram of a front segment and a middle segment of the heart bottom model which have been stretched and smoothed according to an example of the present disclosure.
Figure 9:
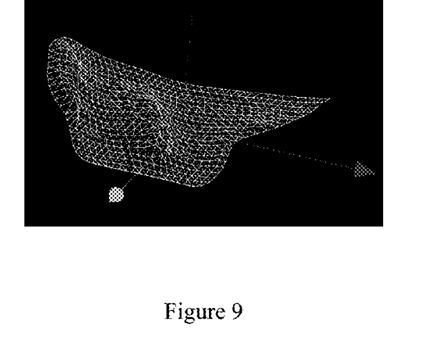
FIG. 9 is a three-dimensional schematic diagram of a rear segment of the heart bottom model which have been stretched and smoothed according to an example of the present disclosure.

For example, as shown in FIG. 7, FIG. 8 and FIG. 9, FIG. 7 is a three-dimensional schematic diagram of a front segment and a middle segment of the heart bottom model which have been stretched according to present disclosure; FIG. 8 is a three-dimensional schematic diagram of a front segment and a middle segment of the heart bottom model which have been stretched and smoothed according to present disclosure; and FIG. 9 is a three-dimensional schematic diagram of a rear segment of the heart bottom model which has been stretched and smoothed according to present disclosure.

Figure 10:
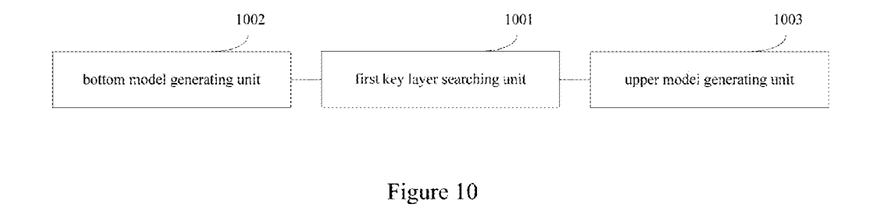
FIG. 10 is a schematic structural diagram of a three-dimensional cardiac image segmentation apparatus according to an example of the present disclosure.

FIG. 10 is a schematic structural diagram of logic of a three-dimensional cardiac image segmentation which is run on a CT apparatus according to present disclosure. Wherein said CT apparatus includes a processor and a non-transitory computer readable storage medium. Instructions are stored on said non-transitory computer readable storage medium. When executed by the processor, the instructions cause said CT apparatus to implement said logic. Based on the functions, said logic includes: a first key layer searching unit 1001, a bottom model generating unit 1002 and an upper model generating unit 1003. In an example, said processor of the CT apparatus read the instructions of the corresponding unit of said logic to:

search a layer of cardiac CT image located between a heart bottom portion and a heart upper portion from layers of cardiac computerized tomography CT images, and the layer of cardiac CT image being taken as a first key layer.

search a boundary of the heart on the first key layer and be taken as a contour of the heart bottom portion, then generate a curved surface model based on the contour of the heart bottom portion and a lowest point of the heart bottom portion, wherein said curved surface model is taken as a heart bottom mode.

search a boundary of the heart from the layers of cardiac CT images above the first key layer, wherein the boundary is taken as a contour of the heart upper portion, and generate a curved surface model based on the contour of the heart upper portion, wherein the curved surface model is taken as a heart upper model.

Furthermore, said processor of the CT apparatus read the instructions of the corresponding unit of said logic to said search a layer of cardiac CT image as a second interface layer between a heart top portion and a heart middle portion from layers of cardiac CT images.

Furthermore, said processor of the CT apparatus read the instructions of the corresponding unit of said logic to:

search a boundary of the heart from the second key layer which boundary may be used as a contour of the heart top portion, and generate a plane model to be used as a heart top model based on the contour of the heart top portion; and search a boundary of the heart from cardiac CT images between the first key layer and the second key layer which boundary may be used as the contour of the heart middle portion, and generate a curved surface model to be used as a heart middle model based on the contour of the heart middle portion.

Figure 11:
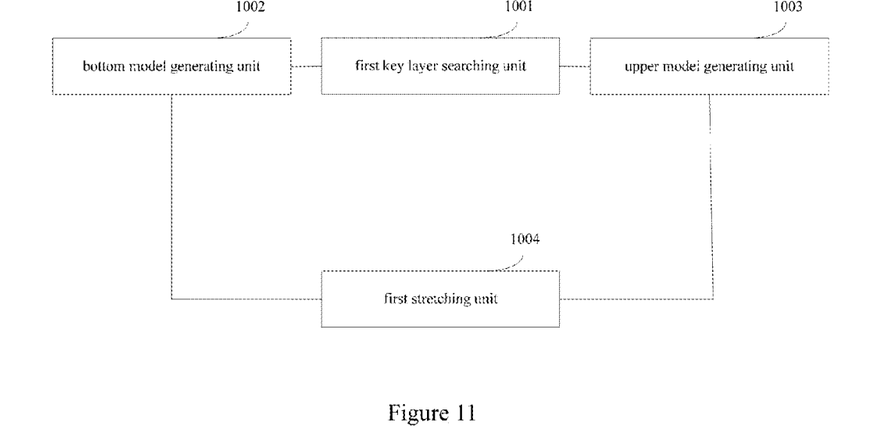
FIG. 11 is a schematic structural diagram of a three-dimensional cardiac image segmentation apparatus according to another example of the present disclosure.

As shown in FIG. 11, based on functions, said logic may further include: a first stretching unit 1004, configured to stretch any one or more models among the heart top model, the heart middle model and the heart bottom model in directions in which a value of an energy function of the model decreases, until the energy function reaches a minimum value.

According to an example of the present disclosure, the logic may further include: a second stretching unit, configured to stretch upwards only a region of the heart top model where a left atrium and a coronary artery are located, and stop stretching the region of the heart top model in the case that top boundaries of the left atrium and the coronary artery are reached.

According to another preferred example of the present disclosure, on the basis of the structure as shown in FIG. 11, before a value of the energy function of the heart middle model reaches a minimum value, the logic may further include: a first determining unit configured to determine whether the heart middle model is stretched to a position where any one of air, a lung, a sternum, or a descending aorta is located, and stop stretching the heart middle model in the case that the heart middle model is stretched to the position where any one of the air, the lung, the sternum, or the descending aorta is located.

According to another example of the present disclosure, on the basis of the structure as shown in FIG. 10, the logic may further include: a second determining unit configured to determine whether the heart bottom model is stretched to a position where any one of a descending aorta or a lung is located, before a value of the energy function of heart bottom model reaches the minimum value; and stop stretching the heart bottom model in the case that the heart bottom model is stretched to the position where any one of the descending aorta or the lung is located.

Figure 12:
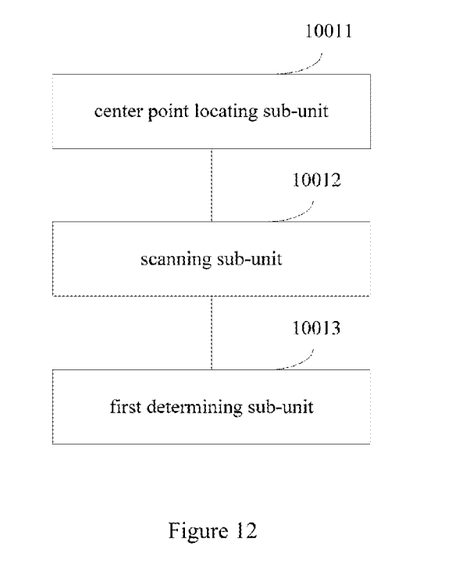
FIG. 12 is a schematic structural diagram of a center point locating sub-unit according to an example of the present disclosure.

According to another example of the present disclosure, as shown in FIG. 12, the above-mentioned first key layer searching unit 1001 may include: a center point locating sub-unit 10011, a scanning sub-unit 10012, a first determining sub-unit 10013. Said processor executes the instructions of the corresponding unit of the logic to:

locate a heart center point in the layers of cardiac CT images;

perform line-by-line scanning on a coronal image where the heart center point is located, and determine whether a lung is detected in a scanned line, scan a next line in the case that the lung is detected in the scanned line, or stop the scanning in the case that no lung is detected in the scanned line; and determine a layer of CT image containing a scanned line where the scanning is stopped as the first key layer between the heart bottom portion and the heart middle portion.

According to another example of the present disclosure, the above-mentioned second key layer searching unit may include: a center point locating sub-unit, and a second determining sub-unit. Said processor executes the instructions of the corresponding unit of the logic to:

locate a heart center point in the layers of cardiac CT images; and determine a cardiac CT image containing the heart center point as the second key layer between the heart top portion and the heart middle portion.

According to another preferred example of the present disclosure, the center point locating sub-unit 10011 may be configured to detect an ascending aorta in the cardiac CT images after aortography is performed on the ascending aorta; and determine a lowest center point of the ascending aorta based on the ascending aorta to be used as a position of a heart valve and label the lowest center point of the ascending aorta as the heart center point.

Besides the structure as shown in FIG. 12, alternatively, according to another example of the present disclosure, the center point locating sub-unit 10011 may be configured to detect a left lung and a right lung on the cardiac CT images; and calculate distances between the left lung and the right lung, select a longest distance, determine a midpoint of the longest distance as a position of a heart valve, and mark the position of the heart valve as the heart center point.

Figure 13:
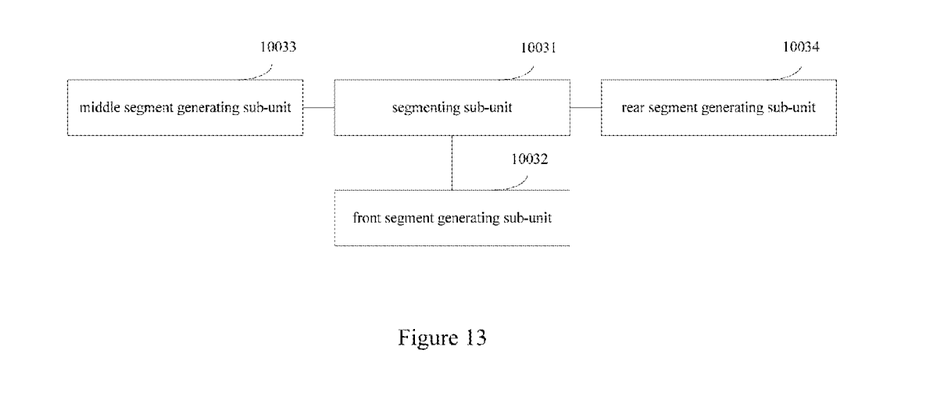
FIG. 13 is a schematic structural diagram of a bottom model generating unit according to an example of the present disclosure.

According to another example of the present disclosure, as shown in FIG. 13, the above-mentioned bottom model generating unit 1003 may include: a segmenting sub-unit 10031, a front segment generating sub-unit 10032, a middle segment generating sub-unit 10033, a rear segment generating sub-unit 10034. Said processor executes the instructions of the corresponding unit of the logic to:

segment the contour of the heart bottom portion into a front segment, a middle segment and a rear segment;

calculate an optimal-cost path between each sampling point on the front segment and the lowest point of the heart bottom portion, and generate a curved surface model based on the optimal-cost path, the curved surface model being taken as a front segment of the heart bottom model;

calculate an optimal-cost path between each pair of sampling points on the middle segment which are symmetrically located in a coronal direction, and generate a curved surface model based on the optimal-cost path, the curved surface model being taken as a middle segment of the heart bottom model; and calculate an optimal-cost path between two sampling points on the middle segment which are symmetrically located in the coronal direction and are closest to the rear segment, and generate a plane model based on the optimal-cost path, the plane model being taken as a rear segment of the heart bottom model.

It can be clearly understood by those skilled in the art that, for convenience and brevity of description, the operational processes of the above described system, apparatus and unit may refer to the corresponding processes according to the aforementioned examples of the method, which are not repeated any more herein.

It should be understood that, in the examples according to the present application, the disclosed system, apparatus and method may be implemented in other ways. The above-mentioned examples of the apparatus according to the discloser are merely illustrative. For example, the division in unit illustrates only a logical division of functions and other kinds of division are possible in practice. For example, multiple units or components may be combined together or may be integrated in another system; or some features may be omitted or not implemented. Furthermore, the coupling or communication connection between the components shown or discussed may be directly coupling, indirectly coupling, or communication connection between apparatuses or units via some keys and may be electrical, mechanical or in other form.

The units described as separate components may be or may be not physically separated. The component presented as a unit may be or may be not a physical unit, i.e. may be located in one place or be distributed on multiple network units, as long as an object of the solutions of the examples can be achieved by some or all of the units.

Furthermore, the functional units in the examples of the disclosure may be all integrated in a processing unit; or the functional units may exist as separate physical units; or two or more of the functional units may be integrated in a unit. The integrated unit may be implemented in the form of hardware or in the form of a software function unit.

It should be noted that, those skill in the art can understand that: all or a few of the blocks for implementing the above examples may be carried out by relevant hardware instructed by programs. The programs may be stored in a non-transitory computer readable storage medium. The programs may implement the processes including the above-mentioned examples of the method, when being executed by a processor. The aforementioned non-transitory storage medium may include a magnetic disk, an optical disk, a read-only memory (ROM), a random access memory (RAM).

The three-dimensional cardiac image segmentation method and apparatus according to the examples of the disclosure are described in details above. The principles and examples of the disclosure are set forth herein by using the examples. The description of the above-mentioned examples is merely for helping understanding the method and the core concept of the disclosure. Moreover, modifications may be made by those skilled in the art to the examples and the field of application in the light of the concept of the disclosure. As a result, the content in the specification should not be construed as limiting the present disclosure.

The invention claimed is:

1. A three-dimensional cardiac image segmentation method, comprising:
   searching from layers of cardiac computerized tomography CT images to obtain a layer of cardiac CT image located between a heart bottom portion and a heart upper portion as a first key layer;
   searching on the first key layer to obtain a first boundary of the heart as a contour of the heart bottom portion, generating a curved surface model based on the contour of the heart bottom portion and a lowest point of the heart bottom portion, and wherein the curved surface model is a heart bottom model; and
   searching layers of cardiac CT images above the first key layer to obtain a plurality of second boundaries of the heart as the contour of the heart upper portion, generating a curved surface model based on the contour of the heart upper portion, and wherein the curved surface model is a heart upper model.

2. The method according to claim 1, further comprising:
   searching from layers of cardiac CT images to obtain a layer of cardiac CT image as a second key layer between a heart top portion and a heart middle portion;
   wherein the searching layers of cardiac CT images above the first key layer to obtain the plurality of second boundaries of the heart as the contour of the heart upper portion, generating a curved surface model based on the contour of the heart upper portion, and wherein the curved surface model is a heart upper model, comprises:
   searching on the second key layer to obtain a third boundary of the heart as a contour of the heart top portion, generating a plane model based on the contour of the heart top portion, and wherein the plane model is a heart top model; searching layers of cardiac CT images between the first key layer and the second key layer to obtain the plurality of third boundaries of the heart as the contour of the heart middle portion, generating a curved surface model based on the contour of the heart middle portion, and wherein the curved surface model is a heart middle model.

3. The method according to claim 2, further comprising:
   stretching any one or more models among the heart top model, the heart middle model and the heart bottom model in directions in which a value of an energy function of the model decreases, until the energy function reaches a minimum value.

4. The method according to claim 2, further comprising:
   stretching upwards only regions of the heart top model where a left atrium and a coronary artery are located, and stopping stretching said regions in the case that top boundaries of the left atrium and the coronary artery are reached.

5. The method according to claim 3, further comprising:
   before the energy function of the heart middle model reaches the minimum value, determining whether the heart middle model is stretched to a position where any one of air, lungs, sternum, or the descending aorta is located, and stopping stretching the heart middle model in the case that the heart middle model is stretched to the position where any one of the air, the lungs, sternum, or the descending aorta is located.

6. The method according to claim 3, further comprising:
   before a value of the energy function of heart bottom model reaches the minimum value, determining whether the heart bottom model is stretched to a position where any one of a descending aorta or a lung is located, and stopping stretching the heart bottom model in the case that the heart bottom model is stretched to the position where any one of the descending aorta or the lung is located.

7. The method according to claim 1, wherein the searching from layers of cardiac computerized tomography CT images to obtain a layer of cardiac CT image located between a heart bottom portion as a first key layer, comprises:
   locating a heart center point in the layers of cardiac CT images;
   performing line-by-line scanning on a coronal image where the heart center point is located, and determining whether a lung is detected in a scanned line, scanning a next line in the case that the lung is detected in the scanned line, or stopping the scanning in the case that no lung is detected in the scanned line; and
   determining a layer of CT image containing a scanned line where the scanning is stopped as the first key layer between the heart bottom portion and the heart middle portion.

8. The method according to claim 2, wherein the searching from layers of cardiac CT images to obtain a layer of cardiac CT image as a second key layer between a heart top portion and a heart middle portion, comprises:
   locating a heart center point in the layers of cardiac CT images; and
   determining a cardiac CT image containing the heart center point as the second key layer between the heart top portion and the heart middle portion.

9. The method according to claim 7, wherein the locating a heart center point in the layers of cardiac CT images, comprises:
   detecting the ascending aorta from the layers cardiac CT images obtained after aortography; and
   determining a lowest center point of the ascending aorta based on the detected ascending aorta, and wherein the lowest center point of the ascending aorta is a position of a heart valve and marking the lowest center point of the ascending aorta as the heart center point.

10. The method according to claim 8, wherein the locating a heart center point in the layers of cardiac CT images, comprises:
    detecting the ascending aorta from the layers cardiac CT images obtained after aortography; and
    determining a lowest center point of the ascending aorta based on the detected ascending aorta, and wherein the lowest center point of the ascending aorta is a position of a heart valve and marking the lowest center point of the ascending aorta as the heart center point.

11. The method according to claim 7, wherein the locating a heart center point in the layers of cardiac CT images comprises:
    detecting a left lung and a right lung on the layers of cardiac CT images; and calculating a distance between the left lung and the right lung, selecting a longest distance, determining a midpoint of the longest distance as a position of a heart valve, and marking the midpoint of the longest distance as the heart center point.

12. The method according to claim 8, wherein the locating a heart center point in the layers of cardiac CT images comprises:
    detecting a left lung and a right lung on the layers of cardiac CT images; and
    calculating a distance between the left lung and the right lung, selecting a longest distance, determining a midpoint of the longest distance as a position of a heart valve, and marking the midpoint of the longest distance as the heart center point.

13. The method according to claim 1, wherein the generating a curved surface model based on the contour of the heart upper portion, and wherein the surface model is a heart upper model, comprises:
    segmenting the contour of the heart bottom portion into a front segment, a middle segment and a rear segment;
    calculating an optimal-cost path between each sampling point on the front segment and the lowest point of the heart bottom portion, generating a curved surface model based on the optimal-cost path, and wherein the curved surface model is a front segment of the heart bottom model;
    calculating an optimal-cost path between each pair of sampling points on the middle segment which are symmetrically located in a coronal direction, generating a curved surface model based on the optimal-cost path, and wherein the curved surface model is a middle segment of the heart bottom model; and
    calculating a optimal-cost path between two sampling points on the middle segment which are symmetrically located in the coronal direction and are closest to the rear segment, generating a plane model based on the optimal-cost path, and wherein the plane model is a rear segment of the heart bottom model.

14. A three-dimensional cardiac image segmentation apparatus comprising a processor and a non-transitory computer readable storage medium storing instructions, wherein when executed by the processor, the instructions cause the apparatus to:
    search from layers of cardiac computerized tomography CT images to obtain a layer of cardiac CT image located between a heart bottom portion and a heart upper portion as a first key layer;
    search on the first key layer to obtain a first boundary of the heart as a contour of the heart bottom portion, generate a curved surface model based on the contour of the heart bottom portion and a lowest point of the heart bottom portion, and wherein the curved surface model is a heart bottom model; and
    search layers of cardiac CT images above the first key layer to obtain a plurality of second boundaries of the heart as a contour of the heart upper portion, generate a curved surface model based on the contours of the heart upper portion, and wherein the curved surface model is a heart upper model.

15. The apparatus according to claim 14, wherein when executed by the processor, the instructions further cause the apparatus to:
    search from layers of cardiac CT images to obtain a layer of cardiac CT image as a second key layer between a heart top portion and a heart middle portion;
    wherein the search layers of cardiac CT images above the first key layer to obtain the plurality of second boundaries of the heart as the contours of the heart upper portion, generate a curved surface model based on the contour of the heart upper portion, and wherein the curved surface model is a heart upper model, comprises:
    search on the second key layer to obtain a third boundary of the heart as a contour of the heart top portion, generate a plane model based on the contour of the heart top portion, and take the plane model as a heart top model; and
    search layers of cardiac CT images between the first key layer and the second key layer to obtain the plurality of third boundaries of the heart as the contours of the heart middle portion, generate a curved surface model based on the contours of the heart middle portion, and wherein the curved surface model is a heart middle model.

16. The apparatus according to claim 15, wherein when executed by the processor, the instructions further cause the apparatus to:
    stretch any one or more models among the heart top model, the heart middle model and the heart bottom model in directions in which a value of an energy function of the model decreases, until the energy function reaches a minimum value.

17. The apparatus according to claim 14, wherein the searching from layers of cardiac computerized tomography CT images to obtain a layer of cardiac CT image located between a heart bottom portion and a heart upper portion, and wherein the layer of cardiac CT image is a first key layer, comprises:
    locating a heart center point in the layers of cardiac CT images;
    performing line-by-line scanning on a coronal image where the heart center point is located, and determining whether a lung is detected in a scanned line, scanning a next line in the case that the lung is detected in the scanned line, or stopping the scanning in the case that no lung is detected in the scanned line; and
    determining a layer of CT image containing a scanned line where the scanning is stopped as the first key layer between the heart bottom portion and the heart middle portion.

18. The apparatus according to claim 15, wherein the searching from layers of cardiac CT images to obtain a layer of cardiac CT image as a second key layer between a heart top portion and a heart middle portion, comprises:
    locating a heart center point in the layers of cardiac CT images; and
    determining a cardiac CT image containing the heart center point as the second key layer between the heart top portion and the heart middle portion.

19. The apparatus according to claim 14, wherein the generating a curved surface model based on the contour of the heart upper portion, and wherein the curved surface model is a heart upper model, comprises:
    segmenting the contour of the heart bottom portion into a front segment, a middle segment and a rear segment;
    calculating an optimal-cost path between each sampling point on the front segment and the lowest point of the heart bottom portion, generating a curved surface model based on the optimal-cost path, and wherein the curved surface model is a front segment of the heart bottom model;

calculating an optimal-cost path between each pair of sampling points on the middle segment which are symmetrically located in a coronal direction, generating a curved surface model based on the optimal-cost path, wherein the curved surface model is a middle segment of the heart bottom model; and calculating an optimal-cost path between two sampling points on the middle segment which are symmetrically located in the coronal direction and are closest to the rear segment, generating a plane model based on the optimal-cost path, and wherein the plane model is a rear segment of the heart bottom model.

* * * * *

UNITED STATES PATENT AND TRADEMARK OFFICE
CERTIFICATE OF CORRECTION

PATENT NO. : 9,795,351 B2  
APPLICATION NO. : 14/830754  
DATED : October 24, 2017  
INVENTOR(S) : Bingsheng Li and Wei He It is certified that error appears in the above-identified patent and that said Letters Patent is hereby corrected as shown below:

In the Claims

In Column 12 Line 20 insert -- and a heart upper portion -- between "between a heart bottom portion" and "as a first key layer"

Signed and Sealed this  
Sixth Day of March, 2018

Andrei Iancu  
*Director of the United States Patent and Trademark Office*